US00PP23750P2

(12) United States Plant Patent
Horvath

(10) Patent No.: US PP23,750 P2
(45) Date of Patent: Jul. 16, 2013

(54) ***GEUM* PLANT NAMED 'ALABAMA SLAMMER'**

(50) Latin Name: ***Geum* hybrid**
Varietal Denomination: Alabama Slammer

(76) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 13/199,629

(22) Filed: Sep. 7, 2011

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Howard Locker

(57) ABSTRACT

A new, distinct *Geum* plant as shown and described, characterized by single to semi-double flowers of orange with red tips.

1 Drawing Sheet

Latin name: *Geum* hybrid.
Cultivar name: 'Alabama Slammer'.

BACKGROUND OF THE INVENTION

The present invention relates to a new and distinct hybrid of *Geum* plant named 'Alabama Slammer' characterized by single to semi-double flowers of orange and red. The new *Geum* was found as a naturally occurring, whole plant sport of 'Tequila Sunrise' U.S. Plant Pat. No. 21,514, patented, in Hebron, Ill. in 2006. The selection of the new plant was due to its' unique and multi colored single to semi-double flowers that have deeper orange petals edged in red compared to the parent plant with yellow petals edged in rose. The initial asexual propagation of the new plant was by division and took place at a nursery in Hebron, Ill. since 2007. Continued asexual propagation by division since that time has shown that the unique features of this new *Geum* plant are stable and reproduced true to type in successive generations.

SUMMARY OF THE INVENTION

In the following description, color references are made to The Royal Horticultural Society Colour Chart (2001). The new *Geum* plant named 'Alabama Slammer' is characterized by single to semi double flowers of orange RHS 44A blending into red RHS N34.

The new *Geum* plant can be compared to the parent *Geum* 'Tequila Sunrise' (U.S. Plant Pat. No. 21,514). The new plant flower colors are orange RHS 44A blending into red RHS N34 while *Geum* 'Tequila Sunrise' has a bicolor flower of yellow RHS 9B blending into 46A.

DESCRIPTION OF PHOTOGRAPHS

Figure 1:
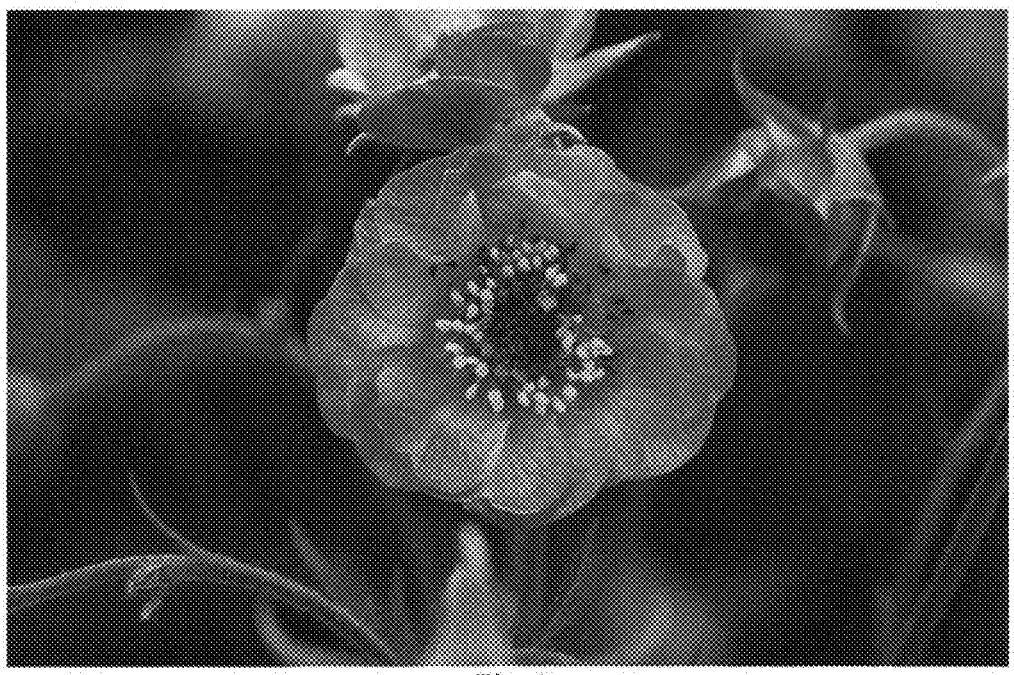
Figure 2:
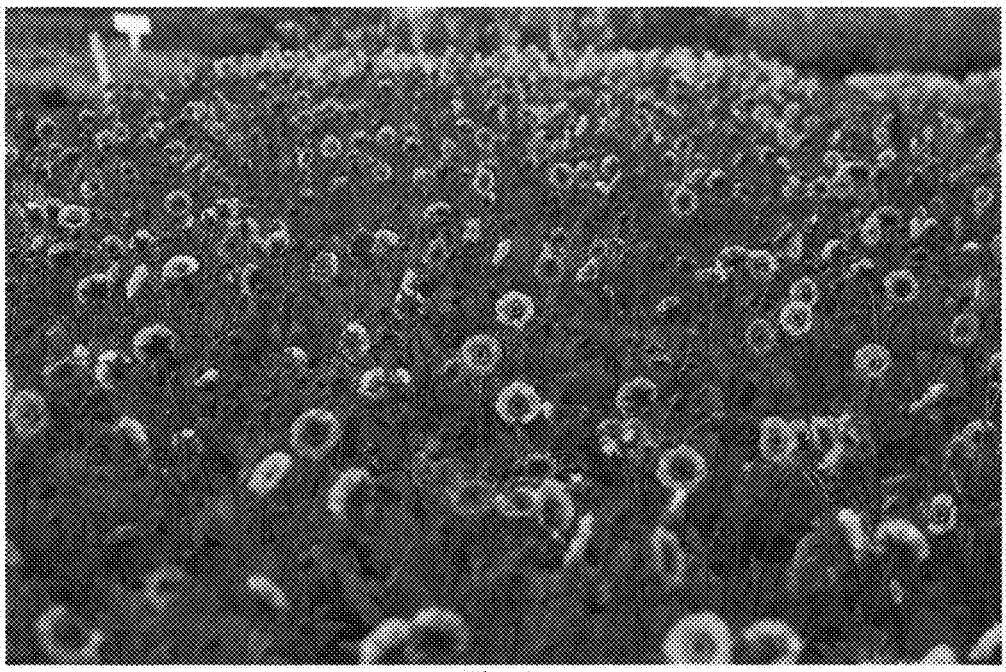

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a field for two years at a nursery in Hebron, Ill. Measurements and numerical values represent averages of typical plants.

Botanical classification: *Geum* hybrid cultivar 'Alabama Slammer'.

Parentage: A sport of *Geum* 'Tequila Sunrise' U.S. Plant Pat. No. 21,514.

Propagation: Vegetative division.

Plant description: Overall habit of the new *Geum* is basal clumps, upright burgundy flower stems topped by single to semi-double flowers that have flowers with orange RHS 44A blending into red RHS N34 at the tips of the petals.

*Plant type*.—Herbaceous perennial.
*Plant height*.—35 cm.
*Plant width*.—30-35 cm.
*Stem*.—Diameter: 3-4 mm.
*Stem or basal branches*.—Length up to 42 cm, with the internode between basal foliage and first leaflet length being 9-11 cm and the second internode between the first leaflet and the second leaflet length being 6-10 cm and the third internode between the second and third leaflet length being 7-8 cm.
*Stem coloration*.—Close to 145A and 145B at the base with the rest of the stem close to N77A.

Foliage description:

*Type*.—Herbaceous.
*Arrangement*.—Basal alternate with typically two or three lateral leaflets per stem.
*Petiole*.—Up to 7-9 cm long, with a diameter of 5 mm, color close to N144.
*Terminal compound leaf length*.—Up to 20 cm.
*Terminal compound leaf width*.—8 cm.
*Terminal leaflet length*.—Typically 4-5 cm.
*Terminal leaflet width*.—Typically 3-4 cm.
*Terminal leaflet shape*.—Obovate with incised margins.
*Terminal and lateral leaf apex*.—Acute.
*Terminal and lateral leaf base*.—Cuneate.
*Terminal and lateral leaf margin*.—Incised.
*Texture*.—Terminal and lateral leaf, upper and lower surfaces: pubescent.
*Venation pattern*.—Terminal and lateral leaf, upper and lower surfaces: pinnate.
*Venation color*.—Terminal and lateral leaf, upper surface is color 137 B and lower surface color is 137 C.

*Lateral leaflet number.*—2 or 3 per stem.
*Lateral leaflet length.*—1-2 cm.
*Lateral leaflet width.*—Up to 1 cm.
*Lateral leaflet shape.*—Obovate.
*Adaxial leaf description.*—Color is 146 A.
*Abaxial leaf description.*—Color 138 B.

Flower description:

*Flower type.*—Corymb.
*Flower color.*—44A at the base and N34 at the tips.
*Flower size.*—Diameter: 25-30 mm across, depth 10-15 mm.
*Flower number.*—4-5 per stem, 90-135 per plant.
*Number flowering stems.*—20-30.
*Bloom period and duration.*—Beginning the first week of May into the first week of June in Hebron, Ill.
*Flower longevity and duration on the plant.*—Approximately 3 weeks.
*Flower longevity and duration cut.*—Approximately one week.
*Individual flower duration.*—Approximately 1 to 2 weeks with petals eventually drying to a tan color.
*Scent.*—None.
*Petal count.*—10-20.
*Petal shape.*—Spatulate.
*Petal arrangement.*—Rotate, overlapping.
*Petal diameter or width.*—12 mm across and petal length — 10 mm long.
*Petal apex.*—Retuse; base: attenuate, margin: entire.
*Petal texture.*—Upper and lower surfaces: smooth, glabrous.
*Petal color.*—Upper surface is color 44A at the base blending into N34 at the tips.
*Petal color.*—Lower surface color is close to 44A at the base blending into N34 at the tips.
*Overall corymb size.*—Diameter and height — 8-12 cm across, 10 cm long.
*Flower buds.*—Diameter: 10-12 mm across, depth: 10 mm, shape: ovoid, surface: slightly pubescent and color between 59A and 59B.
*Sepal size.*—Length: up to 14 mm, diameter: 6 mm at base coming to a point.
*Sepal quantity.*—6.
*Sepal shape.*—Lanceolate, apex: acute, base: cuneate, margin: entire.
*Sepal texture.*—Upper and lower surfaces: Pubescent.
*Sepal color.*—Adaxial color is brown to red-purple. Abaxial color 59 A.
*Peduncle color.*—Purple N 77 A.
*Peduncle size.*—Length: 20-25 mm, diameter: 3 mm.
*Pedicel size.*—Length: 4-8 cm, diameter: 1-2 mm and color N77 A.
*Reproductive organs.*—Stamen — quantity over 100, length 1 cm.
*Anther.*—Quantity: over 100, length: 1 mm, diameter: close to 0.5 mm.
*Pollen.*—Typically present, color: 12A.
*Stigma.*—Number over 50, width less than 1 mm, general color is red.
*Style.*—Number: over 50, length: 6 mm, general color is red.
*Pistil.*—Number: over 50, length: 6+ mm.
*Ovaries.*—Number: over 50 per bloom average, color: is green.
*Fruit.*—Number: over 50 per bloom average, color: is brown, tear shaped, length — 8 mm, width — 2 mm.
*Hardiness.*—USDA zone 4 to 9.

Disease resistance: Resistance to diseases common to *Geum* has not been observed on plants grown under nursery conditions.

I claim:

1. A new, distinct *Geum* plant as shown and described, characterized by single to semi-double flowers of orange with red tips.

* * * * *